(12) United States Patent
Nishijima et al.

(10) Patent No.: US 11,067,506 B2
(45) Date of Patent: Jul. 20, 2021

(54) HYDROGEN DETECTION ELEMENT, METHOD FOR MANUFACTURING HYDROGEN DETECTION ELEMENT, AND HYDROGEN DETECTION DEVICE

(71) Applicants: National University Corporation YOKOHAMA National University, Kanagawa (JP); TOKYO OHKA KOGYO CO., LTD., Kanagawa (JP)

(72) Inventors: Yoshiaki Nishijima, Yokohama (JP); Takeshi Iwai, Kawasaki (JP); Isao Hirano, Kawasaki (JP)

(73) Assignees: NATIONAL UNIVERSITY CORPORATION YOKOHAMA NATIONAL UNIVERSITY, Kanagawa (JP); TOKYO OHKA KOGYO CO., LTD., Kanagawa (JP)

( * ) Notice: Subject to any disclaimer, the term of this patent is extended or adjusted under 35 U.S.C. 154(b) by 0 days.

(21) Appl. No.: 16/495,471

(22) PCT Filed: Mar. 28, 2018

(86) PCT No.: PCT/JP2018/012805
§ 371 (c)(1),
(2) Date: Sep. 19, 2019

(87) PCT Pub. No.: WO2018/181492
PCT Pub. Date: Oct. 4, 2018

(65) Prior Publication Data
US 2020/0088634 A1    Mar. 19, 2020

(30) Foreign Application Priority Data

Mar. 31, 2017 (JP) .............................. JP2017-071285

(51) Int. Cl.
G01N 21/552 (2014.01)
G01N 21/41 (2006.01)
G01N 33/00 (2006.01)

(52) U.S. Cl.
CPC .......... G01N 21/553 (2013.01); G01N 21/41 (2013.01); G01N 33/005 (2013.01)

(58) Field of Classification Search
CPC ..... G01N 21/553; G01N 21/41; G01N 33/005
(Continued)

(56) References Cited

U.S. PATENT DOCUMENTS 7,340,941 B1 * 3/2008 Fruhberger .......... G01N 29/036
422/88
9,651,487 B2 * 5/2017 Smith .................. G02B 5/04
(Continued)

FOREIGN PATENT DOCUMENTS

JP    2005-265590    9/2005
JP    2008-196898    8/2008
(Continued)

OTHER PUBLICATIONS

International Search Report dated Jun. 19, 2018 in International (PCT) Application No. PCT/JP2018/012805.
(Continued)

*Primary Examiner* — Isiaka O Akanbi
(74) *Attorney, Agent, or Firm* — Wenderoth, Lind & Ponack, L.L.P.

(57) ABSTRACT

A hydrogen storage metal is disposed on a base material in a predetermined shape and a predetermined size such that hydrogen is detected based on surface plasmon resonance induced by incident light. The hydrogen storage metal is formed of a film body containing palladium and a noble metal. A spectrum of the light having passed through the hydrogen storage metal in which hydrogen is stored has a
(Continued)

peak in a wavelength band separated from an absorption spectrum C1 of carbon dioxide with respect to the light and an absorption spectra H1 to H3 of water with respect to the light.

12 Claims, 8 Drawing Sheets

(58) Field of Classification Search
USPC .................................................. 356/445–448
See application file for complete search history.

(56) References Cited

U.S. PATENT DOCUMENTS

| | | | | |
|---|---|---|---|---|
| 2006/0065300 | A1* | 3/2006 | Enomoto | H01L 51/4206 136/263 |
| 2008/0212102 | A1 | 9/2008 | Nuzzo et al. | |
| 2008/0218761 | A1* | 9/2008 | Nishikawa | G01N 21/554 356/445 |
| 2009/0280593 | A1* | 11/2009 | Serban | G01N 29/022 438/49 |
| 2012/0105852 | A1* | 5/2012 | Patil | G01N 21/45 356/445 |
| 2012/0113424 | A1* | 5/2012 | Suda | G01N 21/554 356/370 |
| 2016/0054220 | A1 | 2/2016 | Nishijima et al. | |
| 2017/0059403 | A1* | 3/2017 | Froehlich | H01S 5/06804 |
| 2017/0316487 | A1* | 11/2017 | Mazed | G06Q 30/02 |
| 2017/0329439 | A1* | 11/2017 | Jeong | G06F 3/046 |
| 2018/0252658 | A1* | 9/2018 | Ueda | G01N 33/005 |
| 2018/0299458 | A1* | 10/2018 | Gerion | B32B 15/02 |
| 2019/0245155 | A1* | 8/2019 | Heath | H01L 51/0048 |

FOREIGN PATENT DOCUMENTS

| | | |
|---|---|---|
| JP | 2008-216055 | 9/2008 |
| JP | 2014-211362 | 11/2014 |
| JP | 2017-49253 | 3/2017 |
| JP | 2017-062954 | 3/2017 |
| WO | 2011/027899 | 3/2011 |
| WO | 2011/149031 | 12/2011 |

OTHER PUBLICATIONS

Zhao et al., "Annealing enhanced hydrogen absorption in nanocrystalline Pd/Au sensing films", Journal of Applied Physics, vol. 97, Issue 12, 2005, pp. 124301-1 to 24301-7.

Office Action dated Mar. 10, 2020 in Japanese Patent Application No. 2019-509987.

* cited by examiner

HYDROGEN DETECTION ELEMENT, METHOD FOR MANUFACTURING HYDROGEN DETECTION ELEMENT, AND HYDROGEN DETECTION DEVICE

TECHNICAL FIELD

The present invention relates to a hydrogen detection element, a method for manufacturing a hydrogen detection element, and a hydrogen detection device.

Priority is claimed on Japanese Patent Application No. 2017-071285, filed on Mar. 31, 2017, the content of which is incorporated herein by reference.

BACKGROUND ART

In recent years, the use of hydrogen has attracted attention as a new energy source. However, due to the safety concerns and low public awareness of hydrogen, development of a highly reliable hydrogen detection technique has been one of the most important issues in promoting the hydrogen-based industry.

A contact combustion system or a semiconductor system has been frequently used as the hydrogen detection means of the related art, but there is a risk of firing in a case of using any of these systems due to the presence of electrical contacts in a sensor unit, and thus explosion proof measures need to be taken. Therefore, from the viewpoints of being free from the above-described defects and excellent safety, a hydrogen detection system in which the entire sensor unit is formed of an optical system has been studied.

For example, PTL 1 describes a technique of detecting hydrogen by detecting a change in light reflectance or transmittance associated with the hydrogenation using a hydrogen-sensitive dimming mirror. Further, PTL 2 describes a technique of detecting hydrogen by detecting a change in optical frequency characteristics associated with the hydrogen storage using a surface plasmon resonance element configured by forming periodic opening portions in a thin film of palladium serving as a hydrogen storage metal.

CITATION LIST

Patent Literature

[PTL 1] Japanese Unexamined Patent Application, First Publication No. 2005-265590
[PTL 2] PCT International Publication No. WO2011/027899

SUMMARY OF INVENTION

Technical Problem

However, in the above-described techniques of the related art, there is a problem in that absorption and desorption of hydrogen from the hydrogen storage metal takes time. Further, in the above-described techniques of the related art, there is a possibility that the detection accuracy of hydrogen decreases since the quantity of light to be detected varies due to the influence of various substances which are present in an optical path of reflected light or transmitted light.

The present invention has been made in consideration of the above-described circumstances, and an object thereof is to provide a hydrogen detection element which is capable of detecting hydrogen with high accuracy without taking time to carry out absorption and desorption from a hydrogen storage metal, a method for manufacturing the hydrogen detection element, and a hydrogen detection device.

Solution to Problem

According to a first aspect of the present invention, there is provided a hydrogen detection element, in which a hydrogen storage metal is disposed on a base material in a predetermined shape and a predetermined size such that hydrogen is detected based on surface plasmon resonance induced by incident light, in which the hydrogen storage metal is formed of a film body containing palladium and a noble metal, and a spectrum of the light having passed through the hydrogen storage metal in which hydrogen is stored has a peak in a wavelength band separated from an absorption spectrum of carbon dioxide with respect to the light and an absorption spectrum of water with respect to the light.

According to a second aspect of the present invention, there is provided the hydrogen detection element according to the first aspect, in which the hydrogen storage metal is formed into a film having a columnar shape protruding from a surface of the base material.

According to a third aspect of the present invention, there is provided the hydrogen detection element according to the second aspect, in which a plurality of the hydrogen storage metals are arranged at a position of a vertex of an equilateral triangle.

According to a fourth aspect of the present invention, there is provided the hydrogen detection element according to the first aspect, in which the hydrogen storage metal is formed into a film planarly on a surface of the base material and has a plurality of holes arranged to have a predetermined diameter and a predetermined pitch.

According to a fifth aspect of the present invention, there is provided the hydrogen detection element according to the fourth aspect, in which the plurality of holes are arranged at a position of a vertex of an equilateral triangle.

According to a sixth aspect of the present invention, there is provided a hydrogen detection device including: the hydrogen detection element according to any one of the first to fifth aspects of the present invention; a light source unit which emits the light; a light receiving unit which receives the light through the hydrogen detection element; and a detection unit which detects hydrogen based on light reception results of the light receiving unit.

According to a seventh aspect of the present invention, there is provided a method for manufacturing a hydrogen detection element, in which a hydrogen storage metal is disposed on a base material in a predetermined shape and a predetermined size such that hydrogen is detected based on surface plasmon resonance induced by incident light, the method including: forming the hydrogen storage metal in a shape of a film body containing palladium and a noble metal; and forming the hydrogen storage metal such that a peak of a spectrum of the light having passed through the hydrogen storage metal in which hydrogen is stored is in a wavelength band separated from an absorption spectrum of carbon dioxide with respect to the light and an absorption spectrum of water with respect to the light.

According to an eighth aspect of the present invention, there is provided the method for manufacturing a hydrogen detection element according to the seventh aspect of the present invention, in which the hydrogen storage metal is formed into a film by sputtering the palladium and the noble metal in a state in which the base material is heated to a predetermined temperature.

According to a ninth aspect of the present invention, there is provided the method for manufacturing a hydrogen detection element according to the eighth aspect, in which the base material is heated to 250° C. or higher.

According to a tenth aspect of the present invention, there is provided the method for manufacturing a hydrogen detection element according to any one of the seventh to ninth aspects, in which the hydrogen storage metal is formed into a film having a columnar shape protruding from a surface of the base material.

According to an eleventh aspect of the present invention, there is provided the method for manufacturing a hydrogen detection element according to any one of the seventh to ninth aspects, in which the hydrogen storage metal is formed into a film planarly which has a plurality of holes arranged to have a predetermined diameter and a predetermined pitch, on a surface of the base material.

According to a twelfth aspect of the present invention, there is provided the method for manufacturing a hydrogen detection element according to the eleventh aspect, in which the plurality of holes are arranged at a position of a vertex of an equilateral triangle.

Advantageous Effects of Invention

According to the present invention, it is possible to provide a hydrogen detection element which is capable of detecting hydrogen with high accuracy without taking time to carry out absorption and desorption from a hydrogen storage metal, and a hydrogen detection device.

DESCRIPTION OF EMBODIMENTS

Hereinafter, embodiments of a hydrogen detection element, a method for manufacturing the hydrogen detection element, and a hydrogen detection device according to the present invention will be described in detail with reference to FIGS. 1 to 14.

First Embodiment

Figure 1:
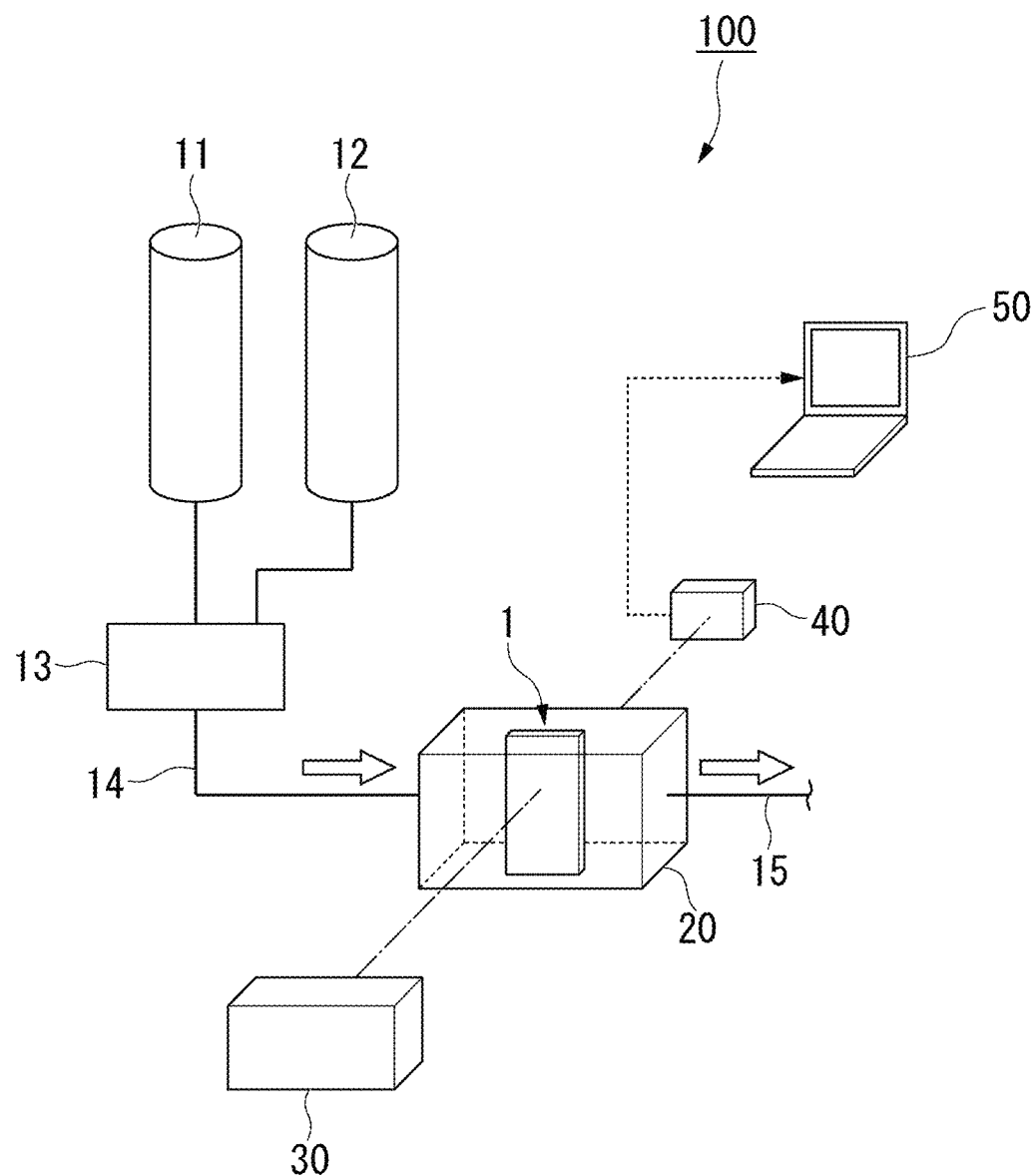
FIG. 1 is a schematic configuration view illustrating a hydrogen detection device 100 which includes a hydrogen detection element 1 according to a first embodiment.

FIG. 1 is a schematic configuration view illustrating a hydrogen detection device 100 which includes a hydrogen detection element 1 according to a first embodiment.

The hydrogen detection device 100 includes the hydrogen detection element 1, a nitrogen supply unit 11, a hydrogen supply unit 12, a mixer 13, a chamber 20, a light source unit 30, a light receiving unit 40, and an arithmetic unit 50.

The mixer 13 mixes nitrogen supplied from the nitrogen supply unit 11 and hydrogen supplied from the hydrogen supply unit 12 at a predetermined mixing ratio (for example, a hydrogen concentration of 4%) and supplies the mixture to the chamber 20 at a predetermined flow rate (for example, 500 mL/h) through a pipe 14. The hydrogen detection element 1 is accommodated in the chamber 20. The pipe 14 to which the mixed gas of nitrogen and hydrogen is introduced and a pipe 15 from which the mixed gas is discharged are connected to the chamber 20.

The light source unit 30 emits light having a predetermined wavelength with respect to the hydrogen detection element 1 in the chamber 20. The light emitted by the light source unit 30 is, for example, infrared light. The light receiving unit 40 receives light which is emitted by the light source unit 30 and passes through the hydrogen detection element 1. The light receiving unit 40 according to the present embodiment receives light transmitted through the hydrogen detection element 1. The light receiving unit 40 outputs the light reception results to the arithmetic unit 50. The arithmetic unit 50 performs calculation based on surface plasmon resonance (the details will be described later) from the results of receiving light by the light receiving unit 40 and detects hydrogen.

Figure 2:
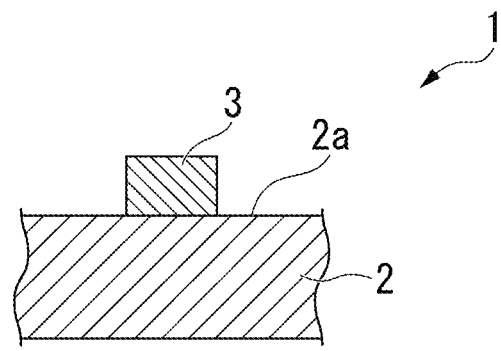
FIG. 2 is a partial cross-sectional view illustrating the hydrogen detection element 1 according to the first embodiment in a thickness direction.
Figure 3:
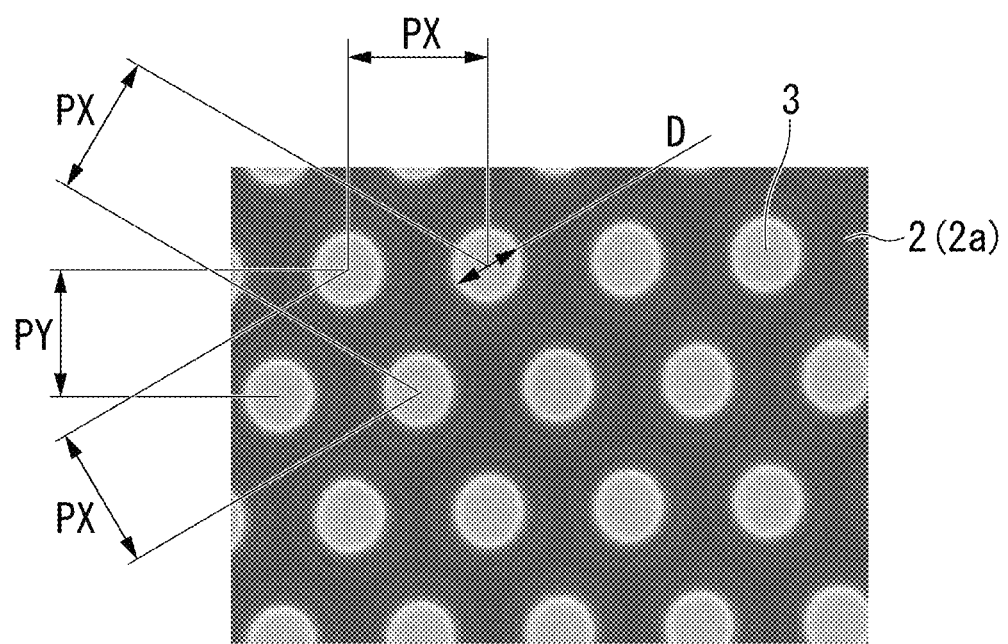
FIG. 3 is a photographic view in which the hydrogen detection element 1 according to the first embodiment is seen in a plan view.

FIG. 2 is a partial cross-sectional view illustrating the hydrogen detection element 1 in the thickness direction. FIG. 3 is a photographic view in which the hydrogen detection element 1 is seen in a plan view.

As illustrated in FIG. 2, the hydrogen detection element 1 includes the hydrogen storage metal 3 disposed on a surface 2a of a base material 2. The base material 2 is formed of, for example, a silicon wafer.

The hydrogen storage metal 3 is a film body formed in a columnar shape with a diameter D which protrudes from the surface 2a. The hydrogen storage metals 3 are arranged in a large cycle (pitch) PX (PX>D) greater than the diameter D in one direction (the horizontal direction in FIG. 3) along the surface 2a. Further, the hydrogen storage metals 3 are arranged at the vertex position of the equilateral triangle having a side with a length of PX. Therefore, in FIG. 3, the columns of the hydrogen storage metals 3 aligned in the horizontal direction are arranged in a cycle PY represented by "√3×PX/2" in the vertical direction in FIG. 3.

The hydrogen storage metal 3 is a material whose dielectric constant (refractive index) is changed at the time of storing hydrogen. In the present embodiment, as an example, hydrogen storage metal 3 is formed of palladium having a film thickness of 50 nm.

The diameter D of the hydrogen storage metal 3 is set according to a target (resonant wavelength) to be detected and is, for example, in a range of 0.5 to 0.9 μm.

The hydrogen storage metal 3 is patterned by, for example, performing a photolithography step. According to one example of the photolithography step, a palladium film is formed on the entire surface 2a of the base material 2 by sputtering or the like, the surface is coated with a negative type photoresist through spin coating or the like, and a region where the hydrogen storage metal 3 is formed in the photoresist is exposed through a mask having opening portions corresponding to the arrangement and the diameters of the plurality of the hydrogen storage metals 3. Thereafter, the hydrogen detection element 1 in which the hydrogen storage metals 3 are patterned in the above-described arrangement is obtained by performing development and etching to remove the palladium film in a region other than the exposed region.

Further, the patterning of the hydrogen storage metal 3 is not limited to the above-described method. For example, the surface 2a of the base material 2 is coated with a positive type photoresist through spin coating or the like, and a region where the hydrogen storage metal 3 is formed in the photoresist is exposed through a mask having opening portions corresponding to the arrangement and the diameters of the plurality of the hydrogen storage metals 3. Further, the photoresist in the region where the hydrogen storage metal 3 is formed by performing development is removed, a palladium film is formed on the entire surface by sputtering or the like, and a lift-off method of removing the palladium film formed on the photoresist is carried out to obtain the hydrogen detection element 1 in which the hydrogen storage metals 3 are patterned in the above-described arrangement.

In the hydrogen detection device 100 with the above-described configuration, the hydrogen detection element 1 is irradiated with infrared light (having a wavelength of 1300 nm or the like) emitted from the light source unit 30, and a part of the infrared light is transmitted through the hydrogen detection element 1 and is incident on the light receiving unit 40. Since hydrogen is supplied to the chamber 20 through the mixer 13, the dielectric constant (refractive index) of the hydrogen storage metal 3 of the hydrogen detection element 1, which is accommodated in the hydrogen detection element 1, is changed by the hydrogen storage metal 3 storing hydrogen.

Figure 4:
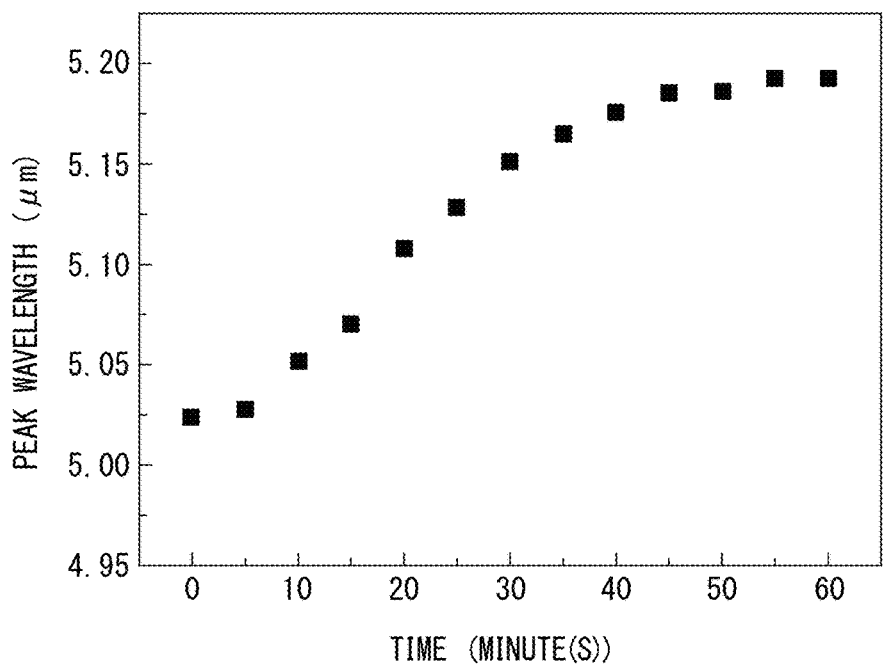
FIG. 4 shows the relationship between the hydrogen storage time of a hydrogen storage metal 3 and the peak value of the wavelength of infrared light transmitted through the hydrogen detection element 1.

FIG. 4 shows the relationship between the hydrogen storage time of the hydrogen storage metal 3 (the elapsed time from the start of hydrogen supply) and the peak value of the wavelength of infrared light transmitted through the hydrogen detection element 1 in which the hydrogen storage metals 3 are arranged in an arrangement pattern of a diameter D of 0.8 μm and a cycle PX of 1.525 μm. As shown in FIG. 4, in a case where hydrogen storage of the hydrogen storage metal 3 proceeds, the peak wavelength of infrared light transmitted through the hydrogen detection element 1 is changed to a long wavelength side. Further, in the case where hydrogen storage of the hydrogen storage metal 3 proceeds, the transmittance (that is, the light quantity of infrared light received by the light receiving unit 40) of infrared light transmitted through the hydrogen detection element 1 is increased compared to a case where hydrogen storage has not been made by the hydrogen storage metal 3.

Figure 5:
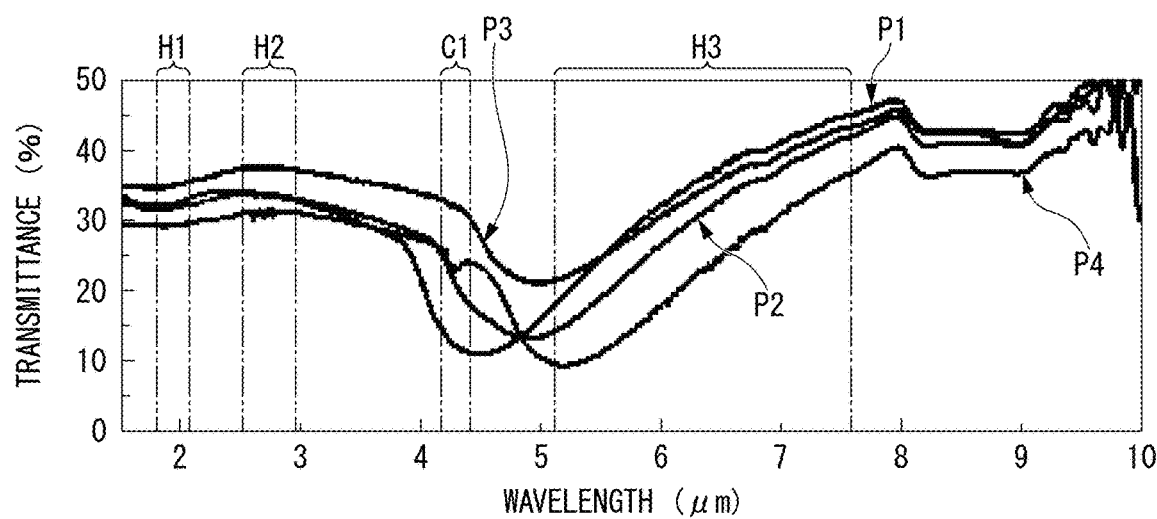
FIG. 5 shows the relationship between the infrared light wavelength and the transmittance in a case where the hydrogen storage metals 3 are arranged in arrangement patterns P1 to P4.

FIG. 5 shows the relationship between the infrared light wavelength and the transmittance in a case where the hydrogen storage metals 3 are arranged in an arrangement pattern P1 of a diameter D of 0.63 μm and a cycle PX of 1.36 μm, a case where the hydrogen storage metals 3 are arranged in an arrangement pattern P2 of a diameter D of 0.68 μm and a cycle PX of 1.41 μm, a case where the hydrogen storage metals 3 are arranged in an arrangement pattern P3 of a diameter D of 0.72 μm and a cycle PX of 1.49 μm, and a case where the hydrogen storage metals 3 are arranged in an arrangement pattern P4 of a diameter D of 0.8 μm and a cycle PX of 1.525 μm as shown in FIG. 4, in the hydrogen detection element 1.

Further, FIG. 5 shows regions H1, H2, and H3 where infrared absorption spectra of water are present and a region C1 where an infrared absorption spectrum of carbon dioxide is present. As shown in FIG. 5, the spectrum of infrared light transmitted through the hydrogen detection element 1 of the arrangement patterns P1 to P4 has a peak in a wavelength band separated from the regions H1, H2, and H3 where the infrared absorption spectra of water are present and the region C1 where the infrared absorption spectrum of carbon dioxide is present. Therefore, during the hydrogen detection, the light receiving unit 40 is capable of receiving infrared light transmitted through the hydrogen detection element 1 in a state in which the influence of light absorption due to water and carbon dioxide contained in the atmosphere in the optical path of the infrared light is suppressed.

The arithmetic unit 50 detects hydrogen according to a difference between the transmittance of infrared light before hydrogen storage in the hydrogen detection element 1 and the transmittance of infrared light after hydrogen storage in the hydrogen detection element 1 based on information obtained by suppressing the influence of light absorption due to water and carbon dioxide to receive light.

As described above, in the hydrogen detection element 1 and the hydrogen detection device 100 according to the present embodiment, hydrogen can be detected with high accuracy in a state in which the influence of light absorption due to water and carbon dioxide contained in the atmosphere in the optical path of the infrared light is suppressed by arranging the hydrogen storage metals 3 in the arrangement pattern (the diameter D and the cycle PX) in which the spectrum of infrared light transmitted through the hydrogen detection element 1 has a peak in a wavelength band separated from the regions H1, H2, and H3 where the infrared absorption spectra of water are present and the region C1 where the infrared absorption spectrum of carbon dioxide is present.

In the above-described embodiment, the configuration in which the infrared light transmitted through the hydrogen detection element 1 is received is employed. However, for example, a configuration in which reflected light or diffracted light from the hydrogen storage metal 3 is received may be employed. In a case where diffracted light is received, in the hydrogen detection element 1 and the hydrogen detection device 100 of the present embodiment, since the intervals between the hydrogen storage metals 3 adjacent to each other are equal regardless of the direction thereof by arranging the hydrogen storage metals 3 at the position of the vertex of an equilateral triangle, diffracted light with a constant cycle is obtained. Therefore, in the hydrogen detection element 1 and the hydrogen detection device 100 according to the present embodiment, hydrogen can be detected with high accuracy without a change in light quantity of diffracted light received at different intervals between the hydrogen storage metals 3 depending on the direction thereof as in a case where the hydrogen storage metals 3 are arranged in a lattice shape.

Second Embodiment

Next, a second embodiment of the hydrogen detection element 1 will be described with reference to FIGS. 6 to 9.

In the first embodiment, the configuration in which the hydrogen storage metal 3 is formed of palladium has been exemplified. However, in the second embodiment, a configuration in which the hydrogen storage metal 3 contains palladium and a noble metal as a catalyst will be described. As the noble metal, gold (Au), silver (Ag), platinum (Pt), or the like can be used. In the present embodiment, a case of using gold will be described.

Figure 6:
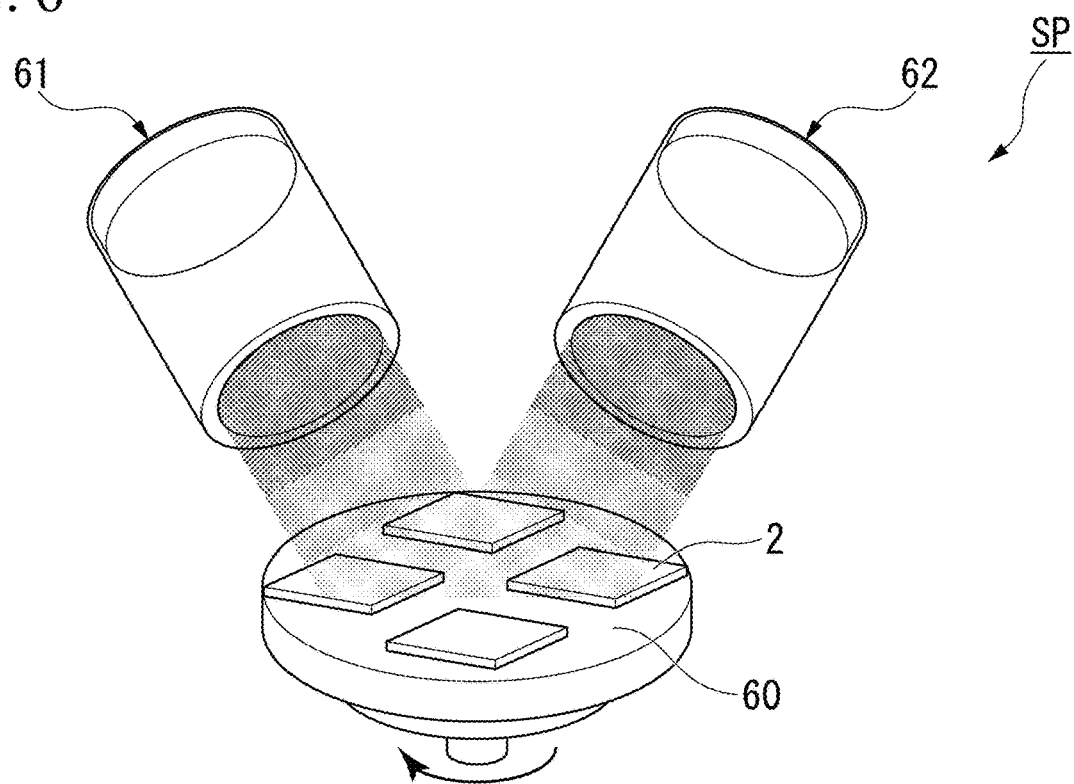
FIG. 6 is a schematic configuration view illustrating a sputtering device SP that forms a hydrogen storage metal according to a second embodiment into a film.

FIG. 6 is a schematic configuration view illustrating a sputtering device SP that forms a hydrogen storage metal into a film on the base material 2. The sputtering device SP includes a substrate holder 60, a palladium sputtering unit 61 having a palladium target, and a gold sputtering unit 62 having a gold target.

A plurality (four sheets in FIG. 6) of base materials 2 are held on the surface of the substrate holder 60 facing the palladium sputtering unit 61 and the gold sputtering unit 62. The substrate holder 60 is rotatable around a shaft parallel to the normal line of the surface facing the palladium sputtering unit 61 and the gold sputtering unit 62.

In the sputtering device SP, a high voltage (for example, 500 eV) is applied to a target for electric discharge in a space filled with inert gas such as argon and the inert gas is atomized to collide with the target. Therefore, the atoms of the target are knocked out and adhered to the substrate 2 to form a film. Further, in the sputtering device SP, palladium and gold are formed into a film on the base material 2 due to rotation of the substrate holder 60.

Palladium and gold are simultaneously formed into a film on the base material 2 by applying a high voltage to both of the palladium target and the gold target. Further, the palladium and the gold are alternately formed into a film on each base material 2 due to rotation of the substrate holder 60, and thus a film body obtained by uniform arrangement of the palladium and the gold as in a case of an alloy. Further, for example, a film body containing the palladium and the gold can be formed at an optional volume ratio or an optional weight ratio by adjusting the voltage applied to the palladium sputtering unit 61 and the gold sputtering unit 62 or the sputtering time. Further, a film body obtained by alternately laminating the palladium layer and the gold layer with a film thickness corresponding to the application time can be formed by alternately applying the voltage to only one of the palladium target and the gold target and adjusting each application time.

Figure 7:
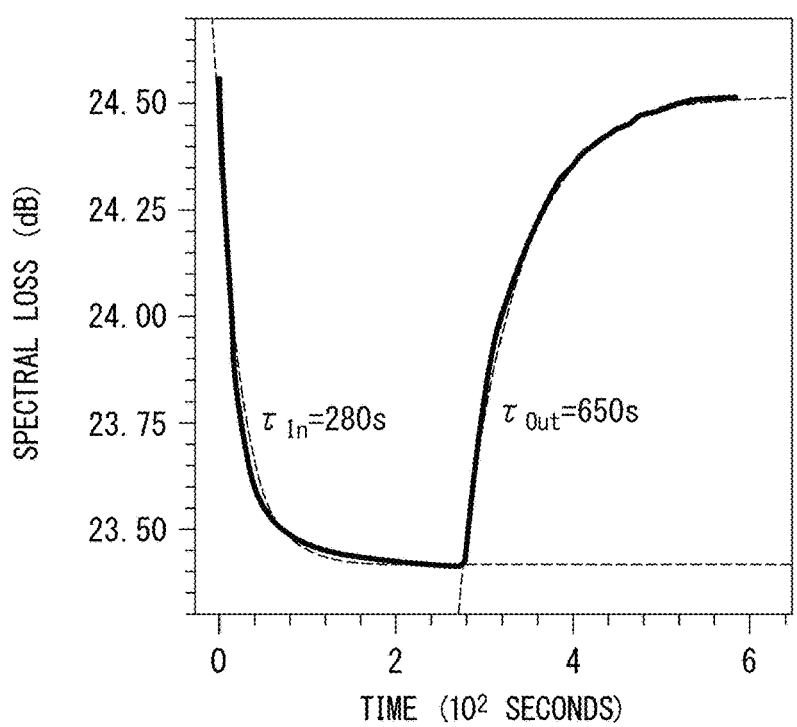
FIG. 7 shows the relationship between the spectral loss and the elapsed time taken for introduction of nitrogen gas after introduction of hydrogen gas into a chamber 20.

FIG. 7 shows the relationship between the spectral loss and the elapsed time taken for introduction of nitrogen gas after introduction of hydrogen gas into the chamber 20 in a case where the hydrogen storage metal 3 contains palladium and gold. FIG. 7 shows the results obtained by introduction of nitrogen gas for 370 seconds from the start of introduction of hydrogen gas to elapse of 650 seconds after introduction of hydrogen gas for 280 seconds from the start of introduction (time: 0 second). As shown in FIG. 7, the spectral loss is decreased and the transmittance of infrared light is increased due to hydrogen storage carried out by the hydrogen storage metal 3 associated with introduction of hydrogen gas into the chamber 20. Thereafter, in a case where nitrogen gas is introduced, it was confirmed that since hydrogen is released from the hydrogen storage metal 3, the spectral loss is increased, and thus the transmittance of infrared light is returned to a level before the introduction of hydrogen gas.

Figure 8:
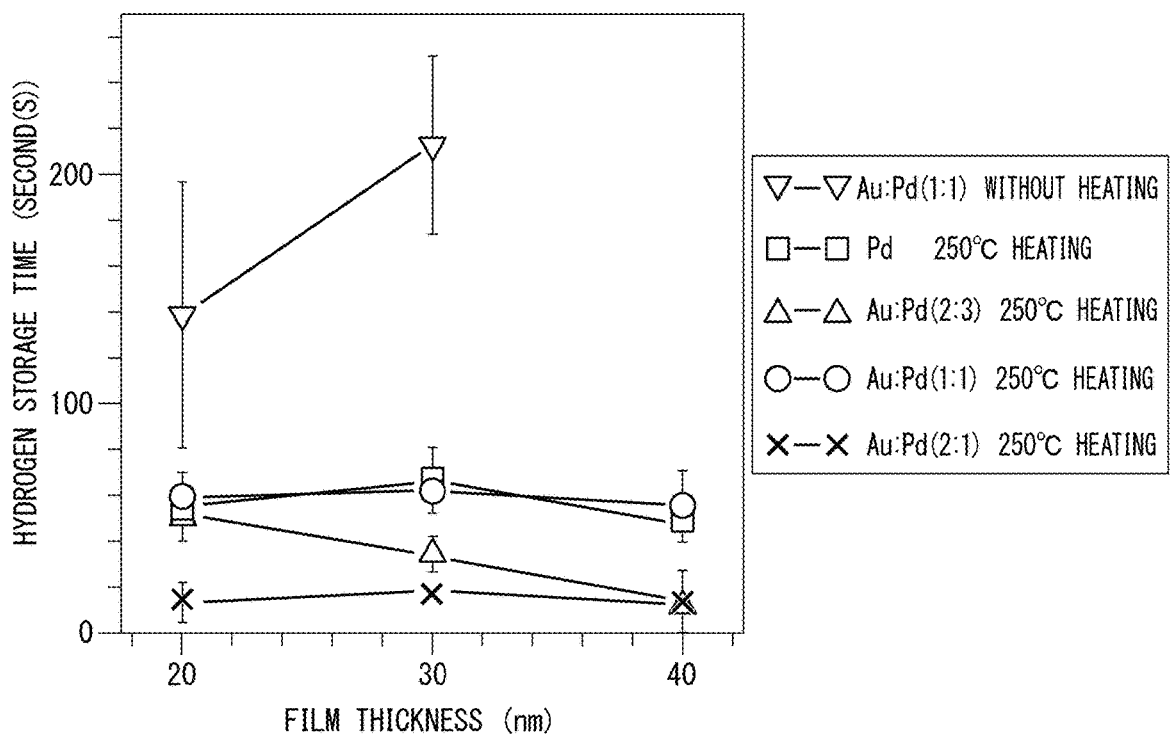
FIG. 8 shows the relationship between the film thickness and the hydrogen storage time in a case where the content ratio between palladium and gold in the hydrogen storage metal 3 is changed.

FIG. 8 shows the relationship between the film thickness and the hydrogen storage time in a case where the content ratio between palladium and gold in the hydrogen storage metal 3 is changed. Further, FIG. 8 shows the relationship between the film thickness and the hydrogen storage time in a case where the base material 2 is heated at 250° C. and a case where the base material 2 is not heated (room temperature), during the formation of palladium and gold into a film. More specifically, the relationship between the film thickness of the hydrogen storage metal 3 and the hydrogen storage time in each of a film body A (the film body A indicated by ⊔-⊔) obtained by forming only palladium into a film in a state in which the base material 2 is heated at 250° C., a film body B (the film body B indicated by ∇-∇) obtained by forming gold and palladium into a film at a content ratio of 1:1 in a state in which the base material 2 is not heated, a film body C (the film body C indicated by ∆-∆) obtained by forming gold and palladium into a film at a content ratio of 2:3 in the state in which the base material 2 is heated at 250° C., a film body D (the film body D indicated by O—O) obtained by forming gold and palladium into a film at a content ratio of 1:1 in the state in which the base material 2 is heated at 250° C., and a film body E (the film body E indicated by x-x) obtained by forming gold and palladium into a film at a content ratio of 2:1 in the state in which the base material 2 is heated at 250° C.

Figure 9:
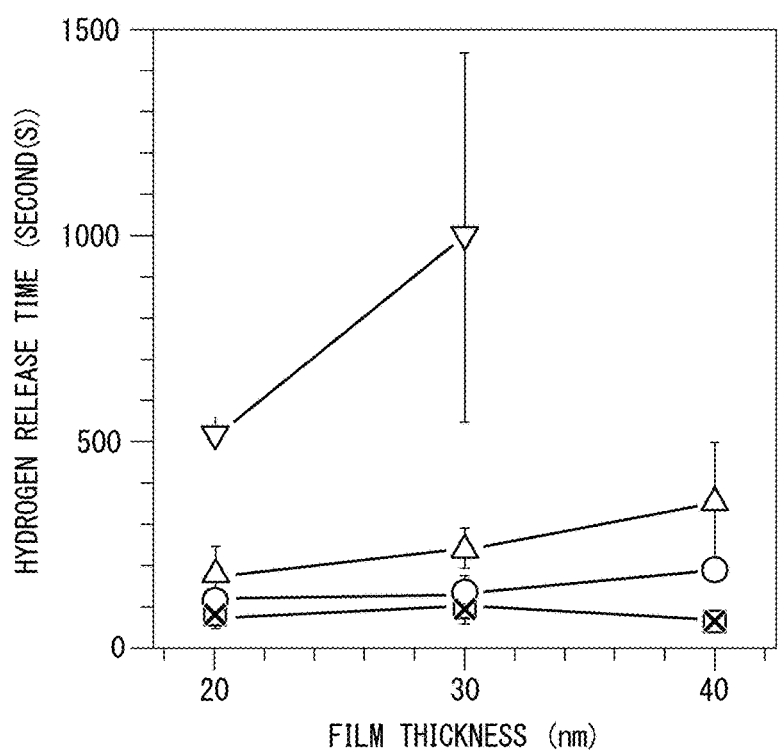
FIG. 9 shows the relationship between the film thickness and the hydrogen release time in the case where the content ratio between palladium and gold in the hydrogen storage metal 3 is changed.

Further, FIG. 9 shows the relationship between the film thickness and the hydrogen release time in the case where the content ratio between palladium and gold in the hydrogen storage metal 3 is changed. Similarly, FIG. 9 also shows the relationship between the film thickness and the hydrogen release time under the above-described five film formation conditions in the case where the base material 2 is heated at 250° C. and the case where the base material 2 is not heated during formation of palladium and gold into a film.

As shown in FIG. 8, it was confirmed that the hydrogen storage time is short and hydrogen can be detected in a short time in a case of the film bodies C and E obtained by forming palladium and gold into a film under the same heating condition compared to the film body A obtained by forming only palladium into a film. Further, it was confirmed that the hydrogen storage time is short and hydrogen can be detected in a short time in a case of the film bodies A, C, D, and E obtained by film formation in the heated state regardless of whether the base material is heated compared to the film body B obtained by film formation in the state in which the base material is not heated.

As shown in FIG. 9, the hydrogen release time becomes equal (film body E) or longer (film bodies B to D) and thus the superiority cannot be confirmed in a case of the film bodies B to E obtained by forming palladium and gold into a film compared to the film body A obtained by forming only palladium into a film. Further, it was confirmed that the hydrogen release time is short and hydrogen release (hydrogen reduction or hydrogen loss) can be detected in a short time in a case of the film bodies A, C, D, and E obtained by film formation in the heated state regardless of whether the base material is heated compared to the film body B obtained by film formation in the state in which the base material is not heated.

Based on the results shown in FIGS. 8 and 9, it was confirmed that the hydrogen detection element 1 in which hydrogen storage and hydrogen release are fast so that hydrogen detection and hydrogen release detection can be performed in a short time is formed in all cases of the film body A obtained by forming only palladium into a film on the hydrogen storage metal 3 and the film bodies C to E obtained by forming palladium and gold into a film in the state in which the base material 2 is heated at 250° C. compared to the film body B obtained by film formation without heating the based material 2.

Further, based on the results shown in FIGS. 8 and 9, it was confirmed that the hydrogen detection element 1 which is capable of rapidly performing hydrogen detection and hydrogen release detection is formed since the hydrogen storage speed and the hydrogen release speed in a case of the film body E obtained by forming gold and palladium into a film at a content ratio of 2:1 are higher than or equal to those of the film body A obtained by forming only palladium.

Third Embodiment

Next, a third embodiment of the hydrogen detection element 1 will be described with reference to FIGS. 10 to 14.

In the first embodiment, the configuration in which the hydrogen storage metal 3 has a columnar shape protruding from the surface of the base material 2 has been described. However, in the third embodiment, a configuration in which the hydrogen storage metal 3 has holes and is planarly formed into a film on the surface 2a of the base material 2 will be described.

Figure 10:
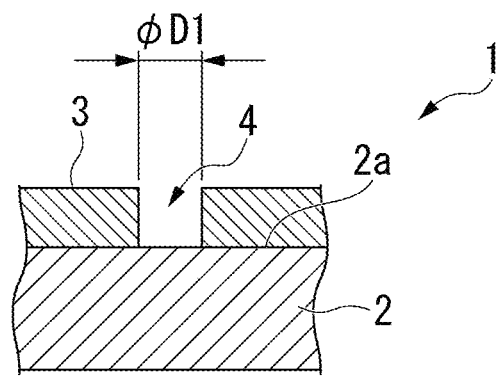
FIG. 10 is a partial cross-sectional view illustrating a hydrogen detection element 1 according to a third embodiment in a thickness direction.
Figure 11:
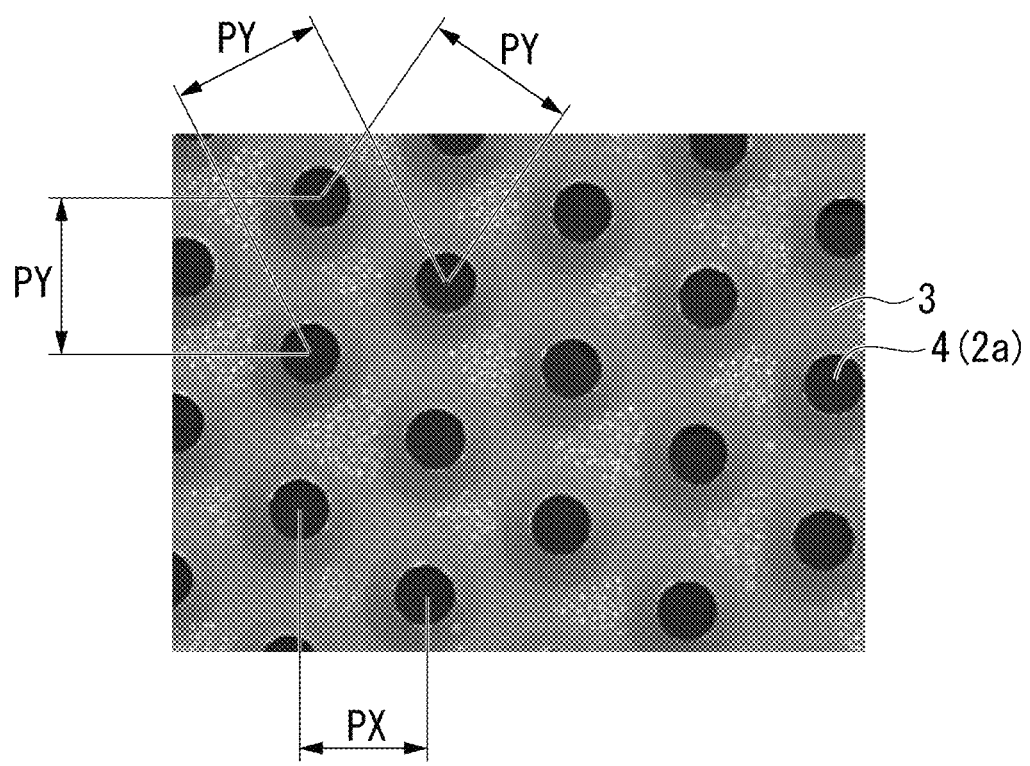
FIG. 11 is a photographic view in which the hydrogen detection element 1 according to the third embodiment is seen in a plan view.

FIG. 10 is a partial cross-sectional view illustrating the hydrogen detection element 1 according to in the thickness direction. FIG. 11 is a photographic view in which the hydrogen detection element 1 is seen in a plan view. In the hydrogen detection element 1 according to the present embodiment, the hydrogen storage metal 3 is planarly formed into a film on the surface 2a of the base material 2. A plurality of holes 4 arranged at a predetermined position are formed in the hydrogen storage metal 3. In other words, the hydrogen storage metal 3 is planarly formed into a film in a region other than the hole 4 on the surface 2a of the base material 2.

The hole 4 is formed to have a circular shape with a diameter D1 in a plan view. As one example, the diameter D1 is in a range of 0.5 to 0.8 µm. The holes 4 are arranged in a cycle (pitch) PY (PY>D) larger than the diameter D1 in a direction along the surface 2a (the vertical direction in FIG. 11). Further, the holes 4 are arranged at the vertex position of an equilateral triangle having a side with a length PY. Accordingly, in FIG. 11, the columns of the holes 4 aligned in the vertical direction are arranged in a cycle PX represented by "$\sqrt{3} \times PY/2$" in the horizontal direction in FIG. 11. As described above, in the hydrogen storage metals 3 in which the holes 4 are arranged in a predetermined cycle with a predetermined diameter D1, light having a characteristic wavelength is transmitted through the holes 4 with the diameter D1 at a sub wavelength based on the surface plasmon resonance characteristics.

The above-described hydrogen storage metals 3 and holes 4 are patterned by performing, for example, a photography step. According to one example of the photography step, a palladium film is formed on the entire surface 2a of the base material 2 by sputtering or the like, the surface 2a thereof is coated with a positive type photoresist through spin coating or the like, and a region where the holes 4 are formed in the photoresist is exposed through a mask having opening portions corresponding to the arrangement and the diameters of the plurality of the holes 4. Thereafter, the hydrogen detection element 1 in which the holes 4 are patterned in the hydrogen storage metal 3 in the above-described arrangement is obtained by performing development and etching to remove the palladium film at the position of the holes 4.

Further, according to the present embodiment, the patterning of the hydrogen storage metal 3 and the holes 4 is not limited to the above-described method, and the above-described lift-off method can be used. For example, the surface 2a of the base material 2 is coated with a negative type photoresist through spin coating or the like, and a region where the holes 4 are formed in the photoresist is exposed through a mask having opening portions corresponding to the arrangement and the diameters of the plurality of the holes 4. Further, the hydrogen detection element 1 in which the holes 4 are patterned in the hydrogen storage metal 3 in the above-described arrangement using the lift-off method of removing the photoresist in a region other than the exposed region (the region where the hydrogen storage metal 3 is formed into a film) due to development, forming a palladium film on the entire surface of the base material by sputtering or the like, and removing the photoresist in the region where the holes 4 are formed and the palladium film formed on the photoresist using an organic solvent or the like.

Figure 12:
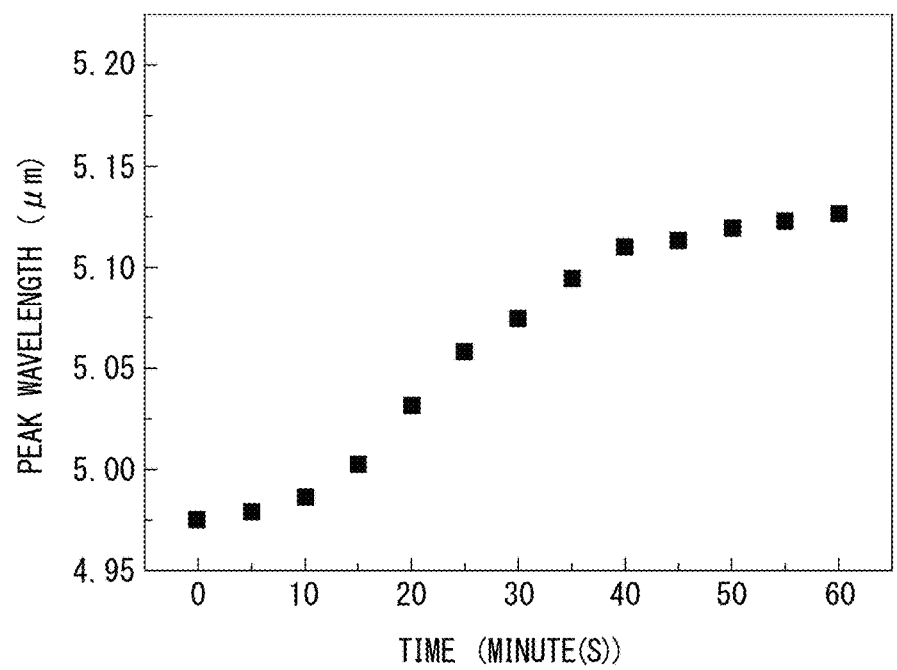
FIG. 12 shows the relationship between the hydrogen storage time of a hydrogen storage metal 3 (formed of palladium) according to the third embodiment and the peak value of the wavelength of infrared light transmitted through the hydrogen detection element 1.

FIG. 12 shows the relationship between the hydrogen storage time (the elapsed time from the start of hydrogen supply) of the hydrogen storage metal 3 and the peak value of the wavelength of infrared light transmitted through the hydrogen detection element 1 in which the holes 4 are arranged in the hydrogen storage metal 3 in an arrangement pattern of a diameter D1 of 0.65 µm and a cycle PY of 1.525 µm. Here, the hydrogen storage metal 3 (formed of palladium) is formed of a film body obtained by forming only palladium into a film.

As shown in FIG. 12, in a case where hydrogen storage of the hydrogen storage metal 3 (formed of palladium) proceeds, the peak wavelength of infrared light transmitted through the hydrogen detection element 1 is changed to a long wavelength side. Further, in the case where hydrogen storage of the hydrogen storage metal 3 (formed of palladium) proceeds, the transmittance (that is, the light quantity of infrared light received by the light receiving unit 40) of infrared light transmitted through the hydrogen detection element 1 is decreased compared to a case where hydrogen storage has not been made by the hydrogen storage metal 3.

Figure 13:
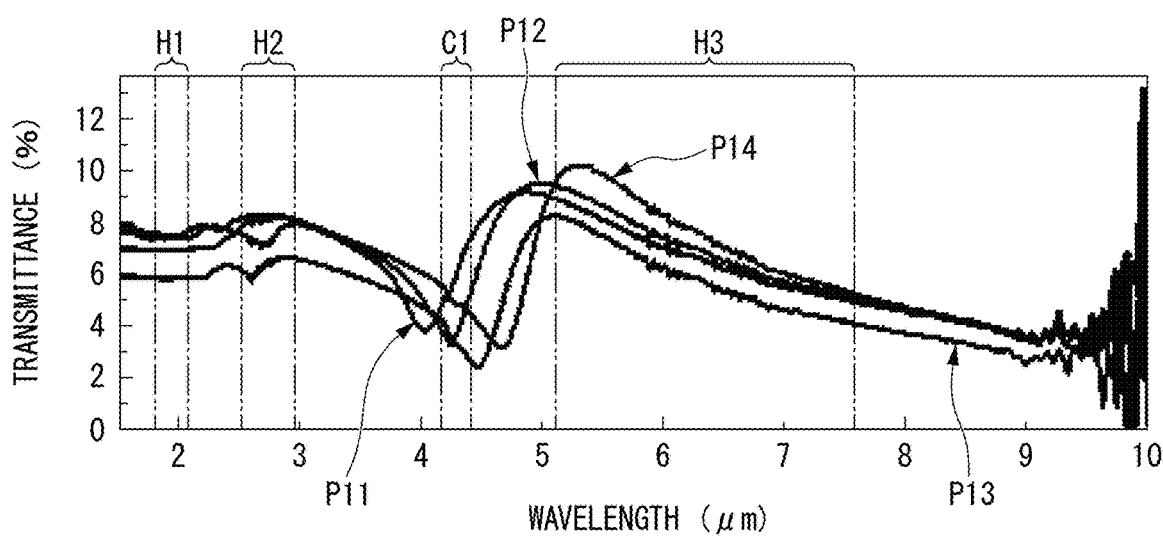
FIG. 13 shows the relationship between the infrared light wavelength and the transmittance in a case where holes 4 are arranged in the hydrogen storage metal 3 (formed of palladium) in arrangement patterns P11 to P14.

FIG. 13 shows the relationship between the infrared light wavelength and the transmittance in a case where the holes 4 are arranged in the hydrogen storage metal 3 in an arrangement pattern P11 of a diameter D of 0.53 µm and a cycle PY of 1.36 µm, a case where the holes 4 are arranged in the hydrogen storage metal 3 in an arrangement pattern P12 of a diameter D of 0.57 µm and a cycle PY of 1.41 µm, a case where the holes 4 are arranged in the hydrogen storage metal 3 in an arrangement pattern P13 of a diameter D of 0.61 µm and a cycle PY of 1.49 µm, and a case where the holes 4 are arranged in the hydrogen storage metal 3 in an arrangement pattern P14 of a diameter D of 0.65 µm and a cycle PY of 1.525 µm as shown in FIG. 12, in the hydrogen detection element 1. The hydrogen storage metal 3 in all cases is formed of a film body obtained by forming only palladium into a film.

FIG. 13 shows regions H1, H2, and H3 where infrared absorption spectra of water are present and a region C1 where an infrared absorption spectrum of carbon dioxide is present. As shown in FIG. 13, the spectrum of infrared light transmitted through the hydrogen detection element 1 of the arrangement patterns P11 to P14 has a peak in a wavelength band separated from the regions H1, H2, and H3 where the infrared absorption spectra of water are present and the region C1 where the infrared absorption spectrum of carbon dioxide is present. Therefore, during the hydrogen detection, the light receiving unit 40 is capable of receiving infrared light transmitted through the hydrogen detection element 1 in a state in which the influence of light absorption due to water and carbon dioxide contained in the atmosphere in the optical path of the infrared light is suppressed.

Figure 14:
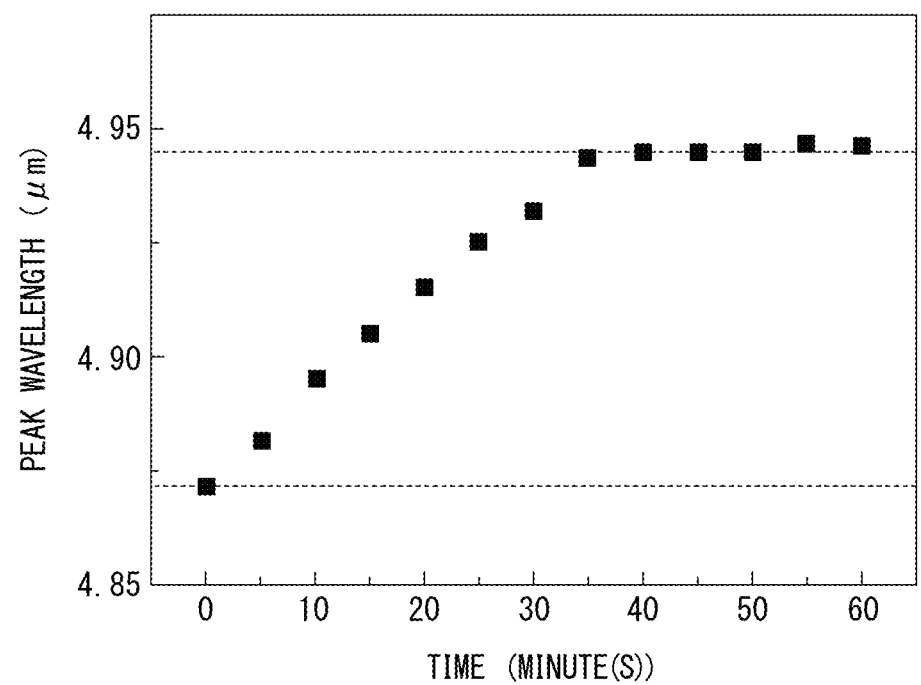
FIG. 14 shows the relationship between the hydrogen storage time of the hydrogen storage metal 3 (formed of palladium) according to the third embodiment and the peak value of the wavelength of infrared light transmitted through the hydrogen detection element 1.

FIG. 14 shows the relationship between the hydrogen storage time (the elapsed time from the start of hydrogen supply) of the hydrogen storage metal 3 and the peak value of the wavelength of infrared light transmitted through the hydrogen detection element 1 in which the holes 4 are arranged in the hydrogen storage metal 3 in an arrangement pattern of a diameter D1 of 0.65 µm and a cycle PY of 1.525 µm. Here, the hydrogen storage metal 3 (formed of palladium) is formed of a film body obtained by forming gold and palladium into a film at a content ratio of 20:80.

The hydrogen storage metal 3 (formed of palladium and gold) and the holes 4 are patterned by performing the same photography step as described above except that only the palladium is changed to palladium and gold.

As shown in FIG. 14, in a case where hydrogen storage of the hydrogen storage metal 3 (formed of palladium) proceeds, the peak wavelength of infrared light transmitted through the hydrogen detection element 1 is changed to a long wavelength side. The amount of change at this time is approximately 80 nm and is decreased compared to the hydrogen storage metal 3 (formed of palladium). Further, the hydrogen storage time of the hydrogen storage metal 3 (formed of palladium and gold) is approximately 30 minutes and is shorter than the case of the hydrogen storage metal 3 (formed of palladium) (approximately 50 minutes). As the result, it was confirmed that hydrogen can be detected in a short time.

Similar to the present embodiment, the arithmetic unit 50 detects hydrogen according to a difference between the transmittance of infrared light before hydrogen storage in the hydrogen detection element 1 and the transmittance of infrared light after hydrogen storage in the hydrogen detection element 1 based on information obtained by suppressing the influence of light absorption due to water and carbon dioxide to receive light.

As described above, according to the present embodiment, in a so-called metal hole array type hydrogen detection element 1 in which a plurality of holes 4 are arranged in the hydrogen storage metal 3, hydrogen can be detected with high accuracy in a state in which the influence of light absorption due to water and carbon dioxide contained in the atmosphere in the optical path of the infrared light is suppressed by arranging the holes 4 in the hydrogen storage metal 3 in an arrangement pattern in which the spectrum of infrared light transmitted through the hydrogen detection element 1 has a peak in a wavelength band separated from the regions H1, H2, and H3 where the infrared absorption spectra of water are present and the region C1 where the infrared absorption spectrum of carbon dioxide is present.

In the present embodiment, since the intervals between the holes 4 adjacent to each other are equal regardless of the direction thereof by arranging the holes 4 at the position of the vertex of an equilateral triangle, for example, hydrogen can be detected with high accuracy without causing a problem of a change in the plasmon resonance characteristics because the intervals of the holes 4 become different from one another depending on the direction thereof as in the case where the holes 4 are arranged in a lattice shape.

Hereinbefore, the preferred embodiments according to the present invention have been described with reference to the accompanying drawings, but the present invention is not limited to such examples. The shapes, the combinations, and the like of each constituent member shown in the above-described examples are merely examples and can be changed based on the design requirements and the like within the range not departing from the scope of the present invention.

For example, according to the first and second embodiments, the configuration in which a plurality of the hydrogen storage metals 3 protruding from the surface 2a of the base material 2 are arranged has been described, but the present invention is not limited to this configuration. For example, a configuration in which a single hydrogen storage metal 3 protruding from the surface 2a of the base material 2 is disposed may be employed.

In regard to the sputtering device SP described in the second embodiment, various types of sputtering methods such as an ion beam method, a magnetron method, an ECR method, and a reactive sputtering method may be applied thereto in addition to the facing target method.

REFERENCE SIGNS LIST

1 . . . hydrogen detection element
2 . . . base material
2a . . . surface
3 . . . hydrogen storage metal
4 . . . hole
100 . . . hydrogen detection device

The invention claimed is:

1. A hydrogen detection element, comprising:
a hydrogen storage metal disposed on a base material in a predetermined shape and a predetermined size such that hydrogen is detected based on surface plasmon resonance induced by incident light,
wherein the hydrogen storage metal is formed of a heated film body containing palladium (Pd) and a noble metal (NM) selected from the group consisting of gold (Au), silver (Ag), and platinum (Pt), in a Pd:NM ratio of 1:2 to 1:1, and
a spectrum of the light having passed through the hydrogen storage metal in which hydrogen is stored has a peak in a wavelength band separated from an absorption spectrum of carbon dioxide with respect to the light and an absorption spectrum of water with respect to the light.

2. The hydrogen detection element according to claim 1, wherein the hydrogen storage metal is formed into a film having a columnar shape protruding from a surface of the base material.

3. The hydrogen detection element according to claim 2, wherein a plurality of the hydrogen storage metals are arranged at a position of the vertex of an equilateral triangle.

4. The hydrogen detection element according to claim 1, wherein the hydrogen storage metal is formed into a film planarly on a surface of the base material and has a plurality of holes arranged to have a predetermined diameter and a predetermined pitch.

5. The hydrogen detection element according to claim 4, wherein the plurality of holes are arranged at a position of a vertex of an equilateral triangle.

6. A hydrogen detection device comprising:
the hydrogen detection element according to claim 1;
a light source which emits the light;
a light receiver which receives the light through the hydrogen detection element; and
a detector which detects hydrogen based on light reception results of the light receiver.

7. A method for manufacturing a hydrogen detection element, in which a hydrogen storage metal is disposed on a base material in a predetermined shape and a predetermined size such that hydrogen is detected based on surface plasmon resonance induced by incident light, the method comprising:
forming the hydrogen storage metal in a shape of a heated film body containing palladium (Pd) and a noble metal (NM) selected from the group consisting of gold (Au), silver (Ag) and platinum (Pt), in a Pd:NM ratio of 1:2 to 1:1;
wherein the hydrogen storage metal is formed such that a peak of a spectrum of the light having passed through the hydrogen storage metal in which hydrogen is stored is in a wavelength band separated from an absorption spectrum of carbon dioxide with respect to the light and an absorption spectrum of water with respect to the light.

8. The method for manufacturing a hydrogen detection element according to claim 7, wherein the hydrogen storage metal is formed into a film by sputtering the palladium and the noble metal in a state in which the base material is heated to a predetermined temperature.

9. The method for manufacturing a hydrogen detection element according to claim 8, wherein the base material is heated to 250° C. or higher.

10. The method for manufacturing a hydrogen detection element according to claim 7, wherein the hydrogen storage metal is formed into a film having a columnar shape protruding from a surface of the base material.

11. The method for manufacturing a hydrogen detection element according to claim 7, wherein the hydrogen storage metal is formed into a film planarly which has a plurality of holes arranged to have a predetermined diameter and a predetermined pitch, on a surface of the base material.

12. The method for manufacturing a hydrogen detection element according to claim 11, wherein the plurality of holes are arranged at a position of a vertex of an equilateral triangle.

* * * * *